US008852564B2

(12) United States Patent
Lebre et al.

(10) Patent No.: US 8,852,564 B2
(45) Date of Patent: Oct. 7, 2014

(54) COSMETIC COMPOSITION COMBINING A COPOLYMER, A NON-VOLATILE OIL AND A GLOSSY OIL

(75) Inventors: Caroline Lebre, Thiais (FR); Sylvie Boulogne, L'Hay les Roses (FR)

(73) Assignee: l'Oreal, Paris (FR)

( * ) Notice: Subject to any disclaimer, the term of this patent is extended or adjusted under 35 U.S.C. 154(b) by 1316 days.

(21) Appl. No.: 11/878,067

(22) Filed: Jul. 20, 2007

(65) Prior Publication Data
US 2008/0025934 A1 Jan. 31, 2008

Related U.S. Application Data

(60) Provisional application No. 60/838,202, filed on Aug. 17, 2006.

(30) Foreign Application Priority Data

Jul. 27, 2006 (FR) ...................... 06 53154

(51) Int. Cl.
*A61Q 1/04* (2006.01)
*A61Q 1/06* (2006.01)
*A61K 8/90* (2006.01)
*A61K 8/81* (2006.01)
*A61K 8/31* (2006.01)

(52) U.S. Cl.
CPC ... *A61K 8/31* (2013.01); *A61K 8/90* (2013.01); *A61Q 1/04* (2013.01); *A61K 8/8111* (2013.01)
USPC ............................................ 424/64; 424/401

(58) Field of Classification Search
None
See application file for complete search history.

(56) References Cited

U.S. PATENT DOCUMENTS

| 6,027,739 | A | * | 2/2000 | Nichols | .................. | 424/401 |
| 2004/0120920 | A1 | | 6/2004 | Lion et al. | | |
| 2005/0095213 | A1 | * | 5/2005 | Blin et al. | .................. | 424/70.11 |
| 2005/0287103 | A1 | * | 12/2005 | Filippi et al. | .................. | 424/70.22 |

FOREIGN PATENT DOCUMENTS

| EP | 1 411 069 A2 | 4/2004 |
| EP | 1 518 534 A2 | 3/2005 |
| EP | 1 604 634 A1 | 12/2005 |
| FR | 2 880 268 A1 | 7/2006 |
| JP | A-2006-151867 | 6/2006 |
| WO | WO 02/34218 A2 | 5/2002 |
| WO | WO 02/067877 A2 | 9/2002 |
| WO | WO 2005/030158 | * 4/2005 |

OTHER PUBLICATIONS

Specific Gravity and Viscosity of Liquid Table; available at http://www.csgnetwork.com/sgvisc.html. Sesame seed oil information originally published Mar. 28, 2002.*

* cited by examiner

*Primary Examiner* — Jyothsna Venkat
(74) *Attorney, Agent, or Firm* — Oliff PLC

(57) ABSTRACT

A cosmetic composition includes, in a physiologically acceptable medium, at least: one copolymer containing at least alkyl methacrylate, alkyl acrylate and acrylic acid monomers; one non-volatile oil having a hydrocarbon-based chain containing at least 16 carbon atoms and having a molar mass of less than 650 g/mol; and one glossy oil having a molar mass of greater than or equal to 650 g/mol.

17 Claims, No Drawings

COSMETIC COMPOSITION COMBINING A COPOLYMER, A NON-VOLATILE OIL AND A GLOSSY OIL

This non provisional application claims the benefit of French Application No. 06 53154 filed on Jul. 27, 2006 and U.S. Provisional Application No. 60/838,202 filed on Aug. 17, 2006.

The present invention relates to a cosmetic composition for caring for and/or making up keratin materials, in particular the lips.

Compositions for making up and/or caring for the skin or the lips conventionally contain a fatty phase based on wax(es) and/or on oil(s), pigments and/or fillers and, optionally, additives such as cosmetic or dermatological active agents.

These compositions are commonly used to give the substrate for which they are intended an aesthetic colour, or even a glossy effect when they are more particularly intended for the lips.

In order to provide this sheen, formulators of cosmetic products generally use oils characterized by a high viscosity and a high refractive index and which also possess good dispersing properties with respect to pigments or fillers when the latter are present in the composition.

In addition to this colour and glossy effect, the user seeks, when using these cosmetic compositions, qualities of comfort and of lengthy resistance.

In fact, the obtaining of these multiple properties, namely gloss, lengthy resistance and comfort, for a makeup can require the superimposition of several compositions, which may or may not be packaged in a single product. Such dual-composition products are in particular described in documents.

For obvious reasons, this need to superimpose two compositions can represent an undesirable constraint.

The aim of the present invention is specifically to provide a new cosmetic product which makes it possible to obtain, in a single act, a makeup which in particular has good comfort properties, good resistance and a glossy effect.

Thus, the inventors have discovered that it is possible to obtain such a composition provided that at least one specific copolymer, a non-volatile oil and a glossy oil, as described hereinafter, are combined therein.

More specifically, according to a first aspect, a subject of the present invention is a cosmetic composition comprising, in a physiologically acceptable medium, at least:
- one copolymer comprising at least alkyl methacrylate, alkyl acrylate and acrylic acid monomers,
- one non-volatile oil that has a hydrocarbon-based chain comprising at least 16 carbon atoms and having a molar mass of less than 650 g/mol, and
- one glossy oil having a molar mass of greater than or equal to 650 g/mol.

A subject of the invention is also a cosmetic process for making up the lips, comprising the application, to a keratin material, and in particular the lips, of a composition as defined above.

A subject of the invention is also the use of a copolymer comprising alkyl methacrylate, alkyl acrylate and acrylic acid monomers in a composition intended to provide a deposit on a keratin material, and in particular the lips, which has good resistance and a satisfactory gloss.

Copolymer

The composition according to the present invention contains at least one copolymer comprising at least alkyl methacrylate, alkyl acrylate and acrylic acid monomers.

According to a first embodiment, the copolymer is derived essentially from monomers chosen from acrylic acid, alkyl methacrylates, alkyl acrylates, and mixtures thereof.

In the above and following text, the term "essentially" is intended to mean comprising at least 85%, preferably at least 90%, better still at least 95%, and even better still 100%.

In this embodiment, the copolymer preferably has a molecular weight of greater than 80 000 g/mol.

The copolymer can advantageously comprise more than 2% by weight of acrylic acid monomers, and in particular from 2% to 15% by weight, for example from 3% to 15% by weight, in particular from 4% to 15% by weight, or even from 5% to 10% by weight, of acrylic acid monomers, relative to the total weight of said copolymer.

As regards the acrylate and methacrylate esters, they can derive from the esterification of linear or branched, cyclic or aromatic $C_1$ to $C_{12}$, in particular $C_4$ to $C_{10}$, alcohols.

By way of non-limiting illustration of these alcohols, mention may in particular be made of isoborneol.

According to one embodiment, said copolymer comprises at least acrylate and methacrylate monomers that derive from the esterification of the same alcohol, and in particular of isoborneol.

According to another embodiment, said copolymer comprises at least monomers of isobutyl acrylate type.

According to a variant of the invention, the copolymer is in the form of a block copolymer, for example comprising at least a first block and at least a second block, the first block being obtained from at least one acrylate monomer of formula $CH_2=CH-COOR_2$ in which $R_2$ represents a $C_4$ to $C_{12}$ cycloalkyl group, and from at least one methacrylate monomer of formula $CH_2=C(CH_3)-COOR'_2$ in which $R'_2$ represents a $C_4$ to $C_{12}$ cycloalkyl group, the second block being obtained from an acrylic acid monomer and from at least one other monomer with a glass transition of less than or equal to 20° C.

According to a preferred embodiment, $R_2$ and $R'_2$ independently or simultaneously represent an isobornyl group.

The term "at least" one block is intended to mean one or more blocks.

The term "block" copolymer is intended to mean a polymer comprising at least two distinct blocks, preferably at least three distinct blocks.

The first block and the second block of the copolymer can advantageously be incompatible with one another.

The expression "blocks incompatible with one another" is intended to mean that the blend formed by a polymer corresponding to the first block and by a polymer corresponding to the second block is not miscible in the polymerization solvent, predominant by weight, for the block copolymer, at ambient temperature (25° C.) and atmospheric pressure ($10^5$ Pa), for a content of the blend of said polymers of greater than or equal to 5% by weight, relative to the total weight of the blend of said polymers and of said polymerization solvent, it being understood that:
  i) said polymers are present in the blend in an amount such that the respective weight ratio ranges from 10/90 to 90/10, and that
  ii) each of the polymers corresponding to the first and second blocks has an average molecular mass (weight-average or number-average) equal to that of the block copolymer +/−15%.

In the case of a mixture of polymerization solvents, should two or more solvents be present in identical proportions by mass, said blend of polymers is immiscible in at least one of them.

Of course, in the case of a polymerization carried out in a single solvent, the latter is the predominant solvent.

Said first and second blocks can be advantageously linked to one another by an intermediate segment comprising at least one monomer that constitutes the first block and at least one monomer that constitutes the second block.

The intermediate segment, which is a block comprising at least one monomer that constitutes the first block and at least one monomer that constitutes the second block of the copolymer, makes it possible to "compatibilize" these blocks.

Advantageously, the intermediate segment comprising at least one monomer that constitutes the first block and at least one monomer that constitutes the second block of the copolymer is a random polymer.

Preferably, the intermediate block is derived essentially from monomers that constitute the first block and the second block.

Advantageously, the intermediate block has a glass transition temperature Tg that is between the glass transition temperatures of the first and second blocks.

The block copolymer of the composition according to the invention is advantageously a film-forming ethylenic block copolymer.

The term "ethylenic" polymer is intended to mean a polymer obtained by polymerization of monomers comprising an ethylenic unsaturation.

The term "film-forming" polymer is intended to mean a polymer capable of forming, on its own or in the presence of an auxiliary film-forming agent, a continuous and adhesive film on a substrate, in particular on the keratin materials.

Preferably, the copolymer does not comprise any silicon atoms in its backbone. The term "backbone" is intended to mean the main chain of the copolymer, as opposed to the pendant sidechains.

Preferably, the copolymer is not water-soluble, i.e. the copolymer is not soluble in water or in a mixture of water and of linear or branched lower monoalcohols having from 2 to 5 carbon atoms, such as ethanol, isopropanol or n-propanol, without modification of pH, at a content of active material of at least 1% by weight, at ambient temperature (25° C.).

The copolymer is preferably not an elastomer.

The term "non-elastomeric copolymer" is intended to mean a polymer which, when it is subjected to a stress intended for stretching it (for example by 30% relative to its initial length), does not return to a length substantially identical to its initial length when the stress stops.

More specifically, the term "non-elastomeric copolymer" denotes a polymer which has an instantaneous recovery ($R_i$<50%) and a delayed recovery ($R_{2h}$<70%) after having undergone an elongation of 30%. Preferably, $R_i$ is <30%, and $R_{2h}$<50%.

More specifically, the non-elastomeric nature of the copolymer is determined according to the following protocol: a film of copolymer is prepared by pouring a solution of the copolymer into a Teflon-coated template and then drying for 7 days in a controlled atmosphere at 23±5° C. and 50±10% relative humidity.

A film approximately 100 μm thick is then obtained, from which are cut rectangular testpieces (for example with a punch) that are 15 mm wide and 80 mm long.

A tensile stress is applied to this sample by means of a device sold under the reference Zwick, under the same temperature and humidity conditions as for the drying.

The testpieces are drawn at a speed of 50 mm/min and the distance between the jaws is 50 mm, which corresponds to the initial length ($I_0$) of the testpiece.

The instantaneous recovery Ri is determined in the following way:
  the testpiece is drawn by 30% ($\epsilon_{max}$), i.e. approximately 0.3 times its initial length ($I_0$),
  the stress is released by applying a return speed equal to the tensile speed, i.e. 50 mm/min, and the percentage residual elongation of the testpiece is measured, after return to a zero constraint ($\epsilon_i$).

The % instantaneous recovery ($R_i$) is given by the following formula:

$$R_i = (\epsilon_{max} - \epsilon_i)/\epsilon_{max} \times 100$$

To determine the delayed recovery, after 2 hours, the residual elongation rate of the testpiece is measured as a percentage ($\epsilon_{2h}$), 2 hours after return to the zero constraint.

The % delayed recovery ($R_{2h}$) is given by the following formula:

$$R_{2h} = (\epsilon_{max} - \epsilon_{2h})/\epsilon_{max} \times 100$$

By way purely of illustration, the copolymer preferably has an instantaneous recovery $R_i$ of 10% and a delayed recovery $R_{2h}$ of 30%.

The polydispersity index of the copolymer is advantageously greater than 2.

The polydispersity index I of the copolymer is equal to the ratio of the weight-average mass Mw to the number-average mass Mn.

The weight-average (Mw) and number-average (Mn) molar masses are determined by gel permeation liquid chromatography (solvent THF, calibration curve established with standards of linear polystyrene, refractometric detector).

The weight-average mass (Mw) of the copolymer is preferably less than or equal to 300 000 g/mol, it ranges, for example, from 35 000 to 200 000 g/mol, and better still from 45 000 to 150 000 g/mol.

The number-average mass (Mn) of the copolymer is preferably less than or equal to 70 000 g/mol, it ranges, for example, from 10 000 to 60 000 g/mol, and better still from 12 000 to 50 000 g/mol.

Preferably, the polydispersity index of the copolymer is greater than 2, for example ranging from 2 to 9, preferably greater than or equal to 2.5, for example ranging from 2.5 to 8, and better still greater than or equal to 2.8, and in particular ranging from 2.8 to 6.

The block copolymer comprises at least a first block and at least a second block.

The first block is advantageously obtained from at least one acrylate monomer of formula $CH_2=CH-COOR_2$ and from at least one methacrylate monomer of formula $CH_2=C(CH_3)-COOR_2$ in which $R_2$ represents a $C_4$ to $C_{12}$ cycloalkyl group. The monomers and the proportions thereof are preferably selected such that the glass transition temperature of the first block is greater than 20° C.

The second block is advantageously obtained from an acrylic acid monomer and from at least one monomer with a glass transition temperature of less than or equal to 20° C.

The monomers and proportions thereof are preferably selected such that the glass transition temperature of the second block is less than or equal to 20° C.

The indicated glass transition temperatures of the first and second blocks can be theoretical Tgs determined from the theoretical Tgs of the monomers that constitute each of the blocks, which can be found in a reference manual such as the Polymer Handbook, 3$^{rd}$ Ed., 1989, John Wiley, according to the following relationship, known as Fox's law: $1/Tg = \Sigma_i (\overline{\omega}_i/Tg_i)$, $\overline{\omega}_i$ being the fraction by mass of the monomer i in the block under consideration and $Tg_i$ being the glass transition temperature of the homopolymer of the monomer i.

Unless otherwise indicated, the Tgs indicated for the first and second blocks of the present application are theoretical Tgs.

The difference between the glass transition temperatures of the first and second blocks is generally greater than 10° C., preferably greater than 20° C., and better still greater than 30° C.

In the present invention, the expression:
"between . . . and . . . " is intended to mean a range of values in which the limits mentioned are excluded, and
the expression:
"from . . . to . . . " and "ranging from . . . to . . . " is intended to mean a range of values in which the limits are included.

First Block

The first block preferably has a Tg of greater than 20° C., for example a Tg ranging from 20 to 170° C., preferably greater than or equal to 50° C., ranging, for example, from 50° C. to 160° C., in particular ranging from 90° C. to 130° C.

According to one embodiment, the first block is obtained from at least one acrylate monomer of formula $CH_2=CH-COOR_2$ in which $R_2$ represents a $C_4$ to $C_{12}$ cycloalkyl group, and from at least one methacrylate monomer of formula $CH_2=C(CH_3)-COOR'_2$ in which $R'_2$ represents a $C_4$ to $C_{12}$ cycloalkyl group.

The first block can be obtained exclusively from said acrylate monomer and from said methacrylate monomer.

The acrylate monomer and the methacrylate monomer are preferably in proportions by mass of between 30:70 and 70:30, preferably between 40:50 and 50:40, in particular of the order of 50:50.

The proportion of the first block advantageously ranges from 20% to 90% by weight relative to the total weight of the copolymer, better still from 30% to 80% by weight, and even better still from 60% to 80% by weight.

According to one embodiment, the first block is obtained by polymerization of isobornyl methacrylate and isobornyl acrylate.

The first block may also comprise:
(meth)acrylic acid, preferably acrylic acid,
tert-butyl acrylate,
methacrylates of formula $CH_2=C(CH_3)-COOR_1$
in which $R_1$ represents a linear or branched, unsubstituted alkyl group containing from 1 to 4 carbon atoms, such as a methyl, ethyl, propyl or isobutyl group,
(meth)acrylamides of formula:

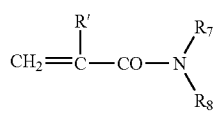

where $R_7$ and $R_8$, which may be identical or different, each represent a hydrogen atom or a linear or branched $C_1$ to $C_{12}$ alkyl group, such as an n-butyl, t-butyl, isopropyl, isohexyl, isooctyl or isononyl group; or $R_7$ represents H and $R_8$ represents a 1,1-dimethyl-3-oxobutyl group, and R' denotes H or methyl. As examples of monomers, mention may be made of N-butylacrylamide, N-t-butylacrylamide, N-isopropylacrylamide, N,N-dimethylacrylamide and N,N-dibutylacrylamide,
and mixtures thereof.

Second Block

The second block advantageously has a glass transition temperature Tg of less than or equal to 20° C., for example a Tg ranging from –100 to 20° C., preferably less than or equal to 15° C., in particular ranging from –80° C. to 15° C., and better still less than or equal to 10° C., for example ranging from –100° C. to 10° C., in particular ranging from –30° C. to 10° C.

The second block is obtained from an acrylic acid monomer and from at least one other monomer having a Tg of less than or equal to 20° C.

The monomer with a glass transition of less than or equal to 20° C. is preferably chosen from the following monomers:
acrylates of formula $CH_2=CHCOOR_3$,
$R_3$ representing an unsubstituted, linear or branched $C_1$ to $C_{12}$ alkyl group, with the exception of the tert-butyl group, in which one or more heteroatoms chosen from O, N and S is (are) optionally intercalated, such as an isobutyl,
methacrylates of formula $CH_2=C(CH_3)-COOR_4$,
$R_4$ representing an unsubstituted, linear or branched $C_6$ to $C_{12}$ alkyl group in which one or more heteroatoms chosen from O, N and S is (are) optionally intercalated,
vinyl esters of formula $R_5-CO-O-CH=CH_2$ where $R_5$ represents a linear or branched $C_4$ to $C_{12}$ alkyl group,
ethers of vinyl alcohol and of a $C_4$ to $C_{12}$ alcohol,
N—($C_4$ to $C_{12}$)alkylacrylamides, such as N-octyl-acrylamide,
and mixtures thereof.

They can preferably be chosen from acrylates of formula $CH_2=CHCOOR_3$, $R_3$ representing an unsubstituted, linear or branched $C_1$ to $C_{12}$ alkyl group, with the exception of the tert-butyl group, in which one or more heteroatoms chosen from O, N and S is (are) optionally intercalated, and in particular with $R_3$ representing isobutyl.

The preferred monomers having a Tg of less than or equal to 20° C. are isobutyl acrylate, 2-ethylhexyl acrylate, or mixtures thereof in any proportions.

Each of the first and second blocks can contain, in a minority proportion, at least one monomer that constitutes the other block.

Thus, the first block can contain at least one monomer that constitutes the second block, and conversely.

Each of the first and/or second blocks can comprise, in addition to the monomers indicated above, one or more other monomers, called additional monomers, that are different from the main monomers mentioned above.

The nature and the amount of this or these additional monomer(s) are chosen in such a way that the block in which they are located has the desired glass transition temperature.

This additional monomer is, for example, chosen from:
monomers with one or more ethylenic unsaturation(s), comprising at least one tertiary amine function, such as 2-vinylpyridine, 4-vinylpyridine, dimethylaminoethyl methacrylate, diethylaminoethyl methacrylate, dimethylaminopropylmethacrylamide, and salts thereof,
methacrylates of formula $CH_2=C(CH_3)-COOR_6$
in which $R_6$ represents a linear or branched alkyl group containing from 1 to 4 carbon atoms, such as a methyl, ethyl, propyl or isobutyl group, said alkyl group being substituted with one or more substituents chosen from hydroxyl groups (such as 2-hydroxypropyl methacrylate or 2-hydroxyethyl methacrylate) and halogen atoms (Cl, Br, I, F), such as trifluoroethyl methacrylate,
methacrylates of formula $CH_2=C(CH_3)-COOR_9$,
$R_9$ representing a linear or branched $C_6$ to $C_{12}$ alkyl group in which one or more heteroatoms chosen from O, N and S is (are) optionally intercalated, said alkyl group being substituted with one or more substituents chosen from hydroxyl groups and halogen atoms (Cl, Br, I, F), acrylates of formula $CH_2=CHCOOR_{10}$,
$R_{10}$ representing a linear or branched $C_1$ to $C_{12}$ alkyl group substituted with one or more substituents chosen from hydroxyl groups and halogen atoms (Cl, Br, I and F), such as 2-hydroxypropyl acrylate and 2-hydroxyethyl acrylate, or $R_{10}$ represents a ($C_1$ to $C_{12}$)alkyl-O-POE (polyoxyethylene) with repetition of the oxyethylene unit from 5 to 30 times, for example methoxy-POE, or $R_8$ represents a polyoxyethylenated group comprising from 5 to 30 ethylene oxide units.

The additional monomer can represent 0.5% to 30% by weight of the weight of the copolymer. According to one embodiment, the copolymer does not contain any additional monomer.

Preferably, the copolymer comprises at least isobornyl acrylate and isobornyl methacrylate monomers in the first block and isobutyl acrylate and acrylic acid monomers in the second block.

Preferably, the copolymer comprises at least isobornyl acrylate and isobornyl methacrylate monomers in equivalent proportion by weight in the first block and isobutyl acrylate and acrylic acid monomers in the second block.

Preferably, the copolymer comprises at least isobornyl acrylate and isobornyl methacrylate monomers in equivalent proportion by weight in the first block, and isobutyl acrylate and acrylic acid monomers in the second block, the first block representing 70% by weight of the copolymer.

Preferably, the copolymer comprises at least isobornyl acrylate and isobornyl methacrylate monomers in equivalent proportion by weight in the first block, and isobutyl acrylate and acrylic acid monomers in the second block, the block with a Tg of greater than 20% representing 70% by weight of the copolymer, and the acrylic acid representing 5% by weight of the copolymer.

According to a preferred embodiment, the copolymer comprises from 50% to 80% by weight of isobornyl methacrylate/acrylate, from 10% to 30% by weight of isobutyl acrylate and from 2% to 10% by weight of acrylic acid, relative to the total weight of the copolymer.

When the copolymer in accordance with the invention comprises at least one acrylic acid monomer, the copolymer can be prepared by means of a process consisting in mixing, in the same reactor, a polymerization solvent, an initiator, an acrylic acid monomer, at least one monomer with a glass transition of less than or equal to 20° C., at least one acrylate monomer of formula $CH_2=CH—COOR_2$ in which $R_2$ represents a $C_4$ to $C_{12}$ cycloalkyl group, and at least one methacrylate monomer of formula $CH_2=C(CH_3)—COOR'_2$ in which $R'_2$ represents a $C_4$ to $C_{12}$ cycloalkyl group, according to the following step sequence:

a portion of the polymerization solvent and a portion of the initiator are run into the reactor, which mixture is heated to a reaction temperature of between 60 and 120° C.,
said at least acrylate monomer of formula $CH_2=CH—COOR_2$ and said at least methacrylate monomer of formula $CH_2=C(CH_3)—COOR'_2$ are subsequently run in, in a first fluid addition, and are left to react for a time T corresponding to a degree of conversion of said monomers of at most 90%,
subsequently, in a second fluid addition, further polymerization initiator, the acrylic acid monomer and said at least monomer with a glass transition of less than or equal to 20° C. are run into the reactor and are left to react for a time T' at the end of which the degree of conversion of said monomers reaches a plateau,
the reaction mixture is brought back to ambient temperature.

The term "polymerization solvent" is intended to mean a solvent or a mixture of solvents. The polymerization solvent can be chosen in particular from ethyl acetate, butyl acetate, alcohols such as isopropanol or ethanol, aliphatic alkanes such as isododecane, and mixtures thereof. Preferably, the polymerization solvent is a mixture of butyl acetate and isopropanol or isododecane.

According to another embodiment, the copolymer can be prepared according to a preparation process consisting in mixing, in the same reactor, a polymerization solvent, an initiator, an acrylic acid monomer, at least one monomer with a glass transition of less than or equal to 20° C., at least one acrylate monomer of formula $CH_2=CH—COOR_2$ in which $R_2$ represents a $C_4$ to $C_{12}$ cycloalkyl group, and at least one methacrylate monomer of formula $CH_2=C(CH_3)—COOR'_2$ in which $R'_2$ represents a $C_4$ to $C_{12}$ cycloalkyl group, according to the following step sequence:

a portion of the polymerization solvent and a portion of the initiator are run into the reactor, which mixture is heated to a reaction temperature between 60 and 120° C.,
subsequently, in a first fluid addition, the acrylic acid monomer and said at least monomer with a glass transition of less than or equal to 20° C. are run in and are left to react for a time T corresponding to a degree of conversion of said monomers of at most 90%,
subsequently, in a second fluid addition, further polymerization initiator, said at least acrylate monomer of formula $CH_2=CH—COOR_2$ and said at least methacrylate monomer of formula $CH_2=C(CH_3)—COOR'_2$ are run into the reactor and left to react for a time T' at the end of which the degree of conversion of said monomers reaches a plateau,
the reaction mixture is brought back to ambient temperature.

The polymerization temperature is preferably of the order of 90° C.

The reaction time after the second fluid addition is preferably between 3 and 6 hours.

The monomers used in the context of this process, and the proportions thereof, may be those described above in the paragraph relating to the copolymer.

The copolymer that goes to make up the composition according to the invention may be the copolymer that can be obtained by means of the process described above.

The composition according to the invention comprises less than 40% by weight of copolymer active material, and advantageously from 5% to 40% by weight, in particular from 5% to 30%, or even from 10% to 20% by weight, relative to the total weight of the composition.

Non-Volatile Oil

The composition according to the invention advantageously comprises a hydrocarbon-based non-volatile oil comprising a chain of at least 16 carbon atoms and having a molar mass of less than 650 g/mol.

The term "hydrocarbon-based" is intended to mean a chain consisting essentially of carbon and of hydrogen and which can contain at least one heteroatom such as an oxygen, a halogen or a nitrogen.

The hydrocarbon-based oil preferably consists of carbon and hydrogen.

The term "oil" is intended to mean a non-aqueous compound that is liquid at ambient temperature (25° C.) and atmospheric pressure (760 mm Hg).

The non-volatile oil according to the invention can in particular comprise an oil having a viscosity between 10 and 300 cPs, preferably between 15 and 200 cPs, and which remains on the skin or the keratin fibre, more generally on the keratin material, at ambient temperature and atmospheric pressure, for at least several hours, and which in particular has a vapour pressure of less than $10^{-3}$ mm Hg (0.13 Pa). This oil subfamily is particularly advantageous in terms of user comfort, in particular with regard to its fluidity. These oils in fact lend themselves to easy and controlled spreading.

The viscosity of the non-volatile oil is measured at 25° C. using the Haake RS75 rheometer equipped with a "60/2°" cone-plate rotor.

Since the viscosity of the oil is relatively low, a plate of 60 mm is selected, as is a rotor of the same diameter, the truncation of which is 200 microns, which corresponds to an angle of 2° (hence the reference 60/2° with respect to the rotor).

An excess amount of oil is deposited on the plate in such a way that the gap (space between the rotor and the plate which is 200 microns thick and 60 mm in diameter) is entirely taken up by said oil.

A stress sweep (for example from $10^{-2}$ to 1000 Pa) is then performed. Since the oil according to the invention is a Newtonian liquid, a constant value is obtained for the viscosity irrespective of the stress exerted.

The oil can more particularly comprise a linear or branched hydrocarbon-based oil having a molar mass of between 100 and 650 g/mol, and more particularly between 200 and 650 g/mol.

By way of non-limiting illustration of these oils, mention may more particularly be made of polyalkenes, and in particular polybutylenes such as Indopol H15®, polydecenes such as Silkflo 366®, alkanes, and in particular squalane such as Phytosqualane®, Sophiderm® or Fitoderm®, or hydrogenated isoparaffins such as Parléam®, isoeicosane, and mixtures thereof.

The non-volatile oil can in particular be squalane.

According to a specific embodiment, the composition according to the invention comprises a combination of squalane and an isobornyl methacrylate/isobornyl acrylate/isobutyl acrylate/acrylic acid copolymer.

The composition according to the invention can comprise from 2% to 50% by weight of non-volatile oil, in particular from 5% to 20%, relative to the total weight of the composition.

Glossy Oil

The composition according to the invention advantageously also comprises a glossy oil other than the non-volatile oil.

The term "glossy oil" is intended to mean an oil able to provide a glossy effect in terms of the composition incorporating it.

In general, the choices of the glossy oil and of the amount thereof in the composition according to the invention can be made so as to provide the composition with an average gloss, measured at 20°, of greater than or equal to 35, for example 40, preferably 45, 55, 60 or 65 out of 100, and/or an average gloss, measured at 60°, of greater than or equal to 65, 70, 75 or 80 out of 100.

The term "average gloss" denotes the gloss as it can be measured using a gloss meter, conventionally as indicated below.

The average gloss is measured at 20° as follows.

A layer of the composition, of between 50 μm and 150 μm thick, is spread on a Leneta contrast card of reference Form 1A Penopac using an automatic spreader. The layer covers at least the white background of the card. The deposit is left to dry for 24 hours at a temperature of 30° C., and then the gloss is measured at 20° on the white background using a Byk Gardner gloss meter of reference microTRI-GLOSS.

This measurement (of between 0 and 100) is repeated at least three times, and the average gloss is the average of the at least three measurements carried out.

The average gloss at 60° is measured in a similar manner, the measurement being carried out at 60° rather than 20°.

The oils that can be used to provide this glossy effect can have a molar mass ranging in particular from 650 to 10 000 g/mol, and preferably from 750 to 7500 g/mol.

The oil of molar mass ranging from 650 to 10 000 g/mol can be chosen from:

lipophilic polymers such as:
  polybutylenes such as Indopol H-100 (of molar mass or MM=965 g/mol), Indopol H-300 (MM=1340 g/mol) or Indopol H-1500 (MM=2160 g/mol), sold or produced by the company Amoco,
  hydrogenated polyisobutylenes such as Panalane H-300 E, sold or produced by the company Amoco (MM=1340 g/mol), Viseal 20 000 sold or produced by the company Synteal (MM=6000 g/mol), or Rewopal PIB 1000 sold or produced by the company Witco (MM=1000 g/mol),
  polydecenes and hydrogenated polydecenes such as: Puresyn 10 (MM=723 g/mol), Puresyn 150 (MM=9200 g/mol) sold or produced by the company Mobil Chemicals,
  vinylpyrrolidone copolymers such as: the vinylpyrrolidone/1-hexadecene copolymer Antaron V-216 sold or produced by the company ISP (MM=7300 g/mol),
esters such as:
  linear fatty acid esters having a total carbon number ranging from 35 to 70, such as pentaerythrityl tetrapelargonate (MM=697.05 g/mol),
  hydroxylated esters such as polyglycerol-2 triisostearate (MM=965.58 g/mol),
  aromatic esters such as tridecyl trimellitate (MM=757.19 g/mol),
  $C_{24}$-$C_{28}$ branched fatty acid or fatty alcohol esters such as those described in application EP-A-0 955 039, and in particular triisoarachidyl citrate (MM=1033.76 g/mol), pentaerythrityl tetraisononanoate (MM=697.05 g/mol), glyceryl triisostearate (MM=891.51 g/mol), glyceryl tridecyl-2-tetradecanoate (MM=1143.98 g/mol), pentaerythrityl tetraisostearate (MM=1202.02 g/mol), polyglyceryl-2-tetraisostearate (MM=1232.04 g/mol) or else pentaerythrityl tetradecyl-2-tetradecanoate (MM=1538.66 g/mol),
silicone oils such as phenyl silicones, for instance Belsil PDM 1000 from the company Wacker (MM=9000 g/mol),
oils of plant origin, such as sesame oil (820.6 g/mol),
and mixtures thereof.

According to a specific embodiment, the composition comprises, as glossy oil, at least one lipophilic polymer, and in particular polybutylene.

According to a specific embodiment, the composition according to the invention comprises a combination of polybutylene and an isobornyl methacrylate/isobornyl acrylate/isobutyl acrylate/acrylic acid copolymer.

The composition according to the invention can have an average gloss, measured at 200, of greater than or equal to 35 and/or an average gloss, measured at 600, of greater than or equal to 65.

The composition according to the invention advantageously contains from 5% to 50% by weight, in particular from 10% to 40% by weight, preferably from 15% to 35% by weight of at least one glossy oil, relative to the total weight of the composition.

Physiologically Acceptable Medium

The term "physiologically acceptable medium" is intended to mean a medium compatible with the keratin materials, such as the organic oils or solvents commonly used in cosmetic compositions.

According to one embodiment, the physiologically acceptable medium comprises at least one fatty substance that is liquid at ambient temperature (25° C. in general). This liquid fatty substance may be of animal, plant, mineral or synthetic origin.

As fatty substances that are liquid at ambient temperature, commonly referred to as oils, that can be used in the invention, mention may be made of: hydrocarbon-based oils of animal origin, such as perhydrosqualene; plant hydrocarbon-based oils such as liquid fatty acid triglycerides containing from 4 to 10 carbon atoms, for instance heptanoic or octanoic acid triglycerides, or else sunflower oil, maize oil, soybean oil, grapeseed oil, sesame oil, apricot oil, macadamia oil, castor oil, avocado oil, caprylic/capric acid triglycerides, jojoba oil, shea butter; linear or branched hydrocarbons of mineral or synthetic origin, such as paraffin oils and derivatives thereof, petroleum jelly; synthetic esters and ethers, in particular of fatty acids, for instance purcellin oil, isopropyl myristate, 2-ethylhexyl palmitate, 2-octyldodecyl stearate, 2-octyldodecyl erucate, isostearyl isostearate; hydroxylated esters such as isostearyl lactate, octyl hydroxystearate, octyldodecyl hydroxylstearate, diisostearyl malate, triisocetyl citrate, heptanoates, octanoates, decanoates of fatty alcohols; polyol esters such as propylene glycol dioctanoate, neopentyl glycol diheptanoate, diethylene glycol diisononanoate; and pentaerythrityl esters; fatty alcohols having from 12 to 26 carbon atoms, such as octyldodecanol, 2-butyloctanol, 2-hexyldecanol, 2-undecylpentadecanol, oleyl alcohol; partially hydrocarbon-based and/or silicone-based fluoro oils; silicone oils such as linear or cyclic, volatile or non-volatile polymethylsiloxanes (PDMSs), for instance cyclomethicones or dimethicones, optionally containing a phenyl group, such as phenyl trimethicones, phenyltrimethylsiloxydiphenylsiloxanes, diphenylmethyldimethyltrisiloxanes, diphenyl dimethicones, phenyl dimethicones, polymethylphenylsiloxanes; and mixtures thereof.

These oils may be present in an amount ranging from 0.01% to 90%, and better still from 0.1% to 85% by weight, relative to the total weight of the composition.

The physiologically acceptable medium of the composition according to the invention can also comprise one or more physiologically acceptable organic solvents (tolerance, toxicology and feel).

The term "polymerization solvent" is intended to mean a solvent or a mixture of solvents. The polymerization solvent for the copolymer according to the invention can be chosen in particular from ethyl acetate, butyl acetate, alcohols such as isopropanol or ethanol, aliphatic alkanes such as isododecane, and mixtures thereof. Preferably, the polymerization solvent for the copolymer is a mixture of butyl acetate and isopropanol, or isododecane.

As solvents that can be used in the composition of the invention, mention may be made, in addition to the polymerization solvents mentioned above, of ketones that are liquid at ambient temperature, such as methyl ethyl ketone, methyl isobutyl ketone, diisobutyl ketone, isophorone, cyclohexanone or acetone; propylene glycol ethers that are liquid at ambient temperature, such as propylene glycol monomethyl ether, propylene glycol monomethyl ether acetate, dipropylene glycol mono-n-butyl ether; short-chain esters (having from 3 to 8 carbon atoms in total) such as ethyl acetate, methyl acetate, propyl acetate, n-butyl acetate or isopentyl acetate; ethers that are liquid at ambient temperature, such as diethyl ether, dimethyl ether or dichlorodiethyl ether; alkanes that are liquid at ambient temperature, such as decane, heptane, dodecane, isododecane or cyclohexane; aromatic cyclic compounds that are liquid at ambient temperature, such as toluene and xylene; aldehydes that are liquid at ambient temperature, such as benzaldehyde, acetaldehyde, and mixtures thereof.

The physiologically acceptable medium can comprise a hydrophilic medium comprising water or a mixture of water and of hydrophilic organic solvent(s) such as alcohols, and in particular linear or branched lower monoalcohols having from 2 to 5 carbon atoms, such as ethanol, isopropanol or n-propanol, and polyols such as glycerol, diglycerol, propylene glycol, sorbitol, pentylene glycol, and polyethylene glycols, or alternatively $C_2$ ethers and $C_2$-$C_4$ aldehydes that are hydrophilic.

The composition according to the invention can also be substantially free of such a hydrophilic medium. The composition according to the invention can comprise less than 5% by weight, or even less than 2% by weight of water relative to the total weight of the composition, and can in particular be anhydrous.

The composition can comprise, in addition to the copolymer described above, an additional polymer such as a film-forming polymer.

According to the present invention, the term "film-forming polymer" is intended to mean a polymer capable of forming, by itself or in the presence of an auxiliary film-forming agent, a continuous and adherent film on a substrate, in particular on the keratin materials.

Among the film-forming polymers that can be used in the composition of the present invention, mention may be made of synthetic polymers of radical type or of polycondensate type, polymers of natural origin, and blends thereof. As film-forming polymer, mention may in particular be made of acrylic polymers, polyurethanes, polyesters, polyamides, polyureas and cellulose polymers such as nitrocellulose.

The polymer can be combined with one or more auxiliary film-forming agents. Such a film-forming agent can be chosen from all the compounds known to those skilled in the art as being capable of performing the desired function, and in particular can be chosen from plasticizers and coalescence agents.

The composition according to the invention can also comprise at least one wax.

For the purpose of the present invention, the term "wax" is intended to mean a lipophilic compound that is solid at ambient temperature (25° C.), that has a reversible solid/liquid state change, and that has a melting point of greater than or equal to 30° C., possibly ranging up to 120° C.

The melting point of the wax can be measured using a differential scanning calorimeter (DSC), for example the calorimeter sold under the name DSC 30 by the company Metler.

The waxes may be hydrocarbon-based, fluoro and/or silicone waxes and may be of plant, mineral, animal and/or synthetic origin. In particular, the waxes have a melting point of greater than 25° C., and better still greater than 45° C.

As wax that can be used in the composition of the invention, mention may be made of beeswax, carnauba wax or candelilla wax, paraffin, microcrystalline waxes, ceresine or ozokerite; synthetic waxes such as polyethylene wax or Fischer-Tropsch wax, silicone waxes such as alkyl dimethicone or alkoxy dimethicone having from 16 to 45 carbon atoms.

The nature and the amount of the solid fatty substances depend on the desired mechanical properties and textures.

By way of indication, the composition can contain from 0% to 50% by weight of waxes, relative to the total weight of the composition and better still from 1% to 30% by weight.

A cosmetic composition in accordance with the present invention can also comprise at least one pasty compound.

The term "pasty compound" is intended to mean in particular a fatty compound which has a reversible solid/liquid state change and contains, at a temperature of 23° C., a liquid fraction and a solid fraction.

The pasty compound can be chosen from:
lanolin and derivatives thereof,
polymeric or non-polymeric silicone compounds,
polymeric or non-polymeric fluoro compounds,
vinyl polymers,
liposoluble polyethers resulting from polyetherification between one or more $C_2$-$C_{100}$, preferably $C_2$-$C_{50}$, diols,
esters,
and mixtures thereof.

The composition according to the invention can also comprise a lipophilic gelling agent.

They may in particular be polymeric or molecular, organic or inorganic, lipophilic gelling agents.

As lipophilic gelling agents, mention may be made of optionally modified clays, such as modified hectorites, hydrophobic treated silica, metal salts of fatty acids, such as aluminium stearates, and mixtures thereof.

The composition according to the invention can also comprise a dyestuff chosen from water-soluble dyes, and pulverulent dyestuffs such as pigments, pearlescent agents and flakes well known to those skilled in the art. The dyestuffs may be present, in the composition, in an amount ranging from 0.01% to 50% by weight, relative to the weight of the composition, preferably from 0.01% to 30% by weight.

The term "pigments" should be understood to mean inorganic or organic, white or coloured particles of any shape that are insoluble in the physiological medium and are intended to colour the composition.

The term "pearlescent agents" should be understood to mean iridescent particles of any shape, in particular produced by certain molluscs in their shell, or else synthesized.

The pigments may be white or coloured, inorganic and/or organic. Among inorganic pigments, mention may be made of titanium dioxide, optionally surface-treated, zirconium oxide or cerium oxide, and also zinc oxide, (black, yellow or red) iron oxide or chromium oxide, manganese violet, ultramarine blue, chromium hydrate and ferric blue, and metal powders such as aluminium powder or copper powder.

Among organic pigments, mention may be made of carbon black, pigments of D & C type, and cochineal/carmine-based, barium-based, strontium-based, calcium-based or aluminium-based lakes.

Mention may also be made of pigments with an effect, such as particles containing a natural or synthetic, organic or inorganic substrate, for example glass, acrylic resins, polyester, polyurethane, polyethylene terephthalate, ceramics or aluminas, said substrate being uncoated or coated with metal substances such as aluminium, gold, silver, platinum, copper or bronze, or with metal oxides such as titanium dioxide, iron oxide, chromium oxide and mixtures thereof.

The pearlescent pigments can be chosen from white pearlescent pigments such as mica coated with titanium or with bismuth oxychloride, coloured pearlescent pigments such as titanium mica coated with iron oxides, titanium mica coated in particular with ferric blue or with chromium oxide, or titanium mica coated with an organic pigment of the above-mentioned type, and also pearlescent pigments based on bismuth oxychloride. Interference pigments, in particular with liquid or multilayer crystals, can also be used.

The water-soluble dyes are, for example, beetroot juice and methylene blue.

The composition according to the invention can also comprise one or more fillers, in particular at a content ranging from 0.01% to 50% by weight, relative to the total weight of the composition, preferably ranging from 0.01% to 30% by weight. The term "fillers" should be understood to mean mineral or synthetic, colourless or white particles of any shape that are insoluble in the medium of the composition irrespective of the temperature at which the composition is produced. These fillers serve in particular to modify the rheology or the texture of the composition.

The fillers may be inorganic or organic of any shape, platelet-shaped, spherical or oblong, irrespective of the crystallographic form (for example, leaflet, cubic, hexagonal, orthorhombic, etc.). Mention may be made of talc, mica, silica, kaolin, polyamide (Nylon®) powders (Orgasol® from Atochem), poly-β-alanine powders and polyethylene powders, tetrafluoroethylene (Teflon®) polymer powders, lauroyl lysine, starch, boron nitride, polymeric hollow microspheres such as those of polyvinylidene chloride/acrylonitrile, for instance Expancel® (Nobel Industrie), or of acrylic acid copolymers (Polytrap® from the company Dow Corning), and silicone resin microbeads (Tospearls® from Toshiba, for example), elastomeric polyorganosiloxane particles, precipitated calcium carbonate, magnesium carbonate, magnesium hydrogen carbonate, hydroxyapatite, hollow silica microspheres (Silica Beads® from Maprecos), glass or ceramic microcapsules, and metal soaps derived from organic carboxylic acids having from 8 to 22 carbon atoms, preferably from 12 to 18 carbon atoms, for example zinc stearate, magnesium stearate, lithium stearate, zinc laurate or magnesium myristate.

The composition according to the invention may in particular be in the form of a suspension, dispersion, solution, gel or emulsion, in particular oil-in-water (O/W) or water-in-oil (W/O) or multiple (W/O/W or polyol/O/W or O/W/O) emulsion, or in the form of a cream, paste, foam, dispersion of vesicles, in particular of ionic or non-ionic lipids, two-phase or multiphase lotion, spray, powder or paste, in particular flexible paste.

Those skilled in the art may choose the appropriate galenic form, and also the method for preparing it, on the basis of their general knowledge, taking into account, firstly, the nature of the constituents used, in particular their solubility in the substrate, and, secondly, the application envisaged for the composition.

The composition according to the invention may be intended for caring for and/or making up keratin materials, in particular the lips and the skin, in particular the lips.

The composition according to the invention may be in the form of a liquid gloss.

The examples which follow illustrate a composition according to the invention in a non-limiting manner.

The amounts are expressed in grams.

EXAMPLES

Example 1

Preparation of a poly(isobornyl acrylate/diisobornyl methacrylate/isobutyl acrylate/acrylic acid) copolymer 300 g of isododecane are introduced in a 1-liter reactor and then the temperature is increased so as to go from ambient temperature (25° C.) to 90° C. in 1 hour.

105 g of isobornyl methacrylate, 105 g of isobornyl acrylate and 1.8 g of 2,5-bis(2-ethylhexanoylperoxy)-2,5-dimethylhexane (Trigonox® 141 from Akzo Nobel) are then added, at 90° C. in 1 hour.

The mixture is maintained at 90° C. for 1 h 30.

75 g of isobutyl acrylate, 15 g of acrylic acid and 1.2 g of 2,5-bis(2-ethylhexanoylperoxy)-2,5-dimethylhexane are then introduced into the above mixture, still at 90° C., and in 30 minutes.

The mixture is maintained at 90° C. for 3 hours and the whole is then cooled.

A solution containing 50% of active material of copolymer in isododecane is obtained.

A copolymer is obtained, comprising a first block or poly(isobornyl acrylate/isobornyl methacrylate) block having a Tg of 128° C., a second poly(isobutyl acrylate/acrylic acid) block having a Tg of −9° C. and an intermediate block which is an isobornyl acrylate/isobornyl methacrylate/isobutyl acrylate/acrylic acid random copolymer.

The Tg of the copolymer is 74° C.

These are theoretical Tgs calculated by means of Fox's law.

Example 2

Formulation of Liquid Gloss Type

The procedure for 200 g of the following formulation is the following:

The pigments are ground 3 times, in a three-roll mill, in octyldodecanol brought beforehand to 60° C. The ground material is left to cool to ambient temperature (25° C.) in a jacketed heating pan or in a beaker.

The copolymer, the squalane, the polybutylene, the pearlescent agents and the fragrance are added to the ground material. The whole is stirred using a turbine mixer (type: Rayneri) in order to homogenize.

When the mixture is homogeneous, the polyphenyl-trimethylsiloxydimethylsiloxane is added with stirring at 800 rpm with the Rayneri over approximately 30 minutes.

Finally, fumed silica is added gradually and stirring with the turbine mixer is maintained at 1000 rpm for 20 minutes.

| NAME | Concentration (% by weight) |
| --- | --- |
| Refined plant perhydrosqualene (INCI name = squalene) | 10.86 |
| 2-Octyldodecanol | 15.39 |
| Rutile titanium oxide treated with alumina/silica/trimethylolpropane | 2.74 |
| RED 7 | 0.54 |
| Lake Blue 1 | 0.16 |
| Lake Yellow 6 | 2.58 |
| Black iron oxide | 0.25 |
| Mica-titanium dioxide-brown iron oxide | 2 |
| Polyphenyltrimethylsiloxydimethylsiloxane[1] | 20.03 |
| Hydrophobic fumed silica surface-treated with dimethylsilane[3] | 4.5 |
| Poly(isobornyl methacrylate-co-isobornyl acrylate-co-isobutyl acrylate-co-acrylic acid) at an active material content of 50% in isododecane | 30 |
| Polybutylene[2] | 10.65 |
| Fragrance | 0.3 |
| Total | 100 |

[1]Belsil PDM 1000 from Wacker (viscosity 1000 cPs MW:9000)
[2]Indopol H 100 (MW: 920)
[3]Aerosil R 972 from Degussa This gloss composition, applied to the lips in a single movement, has satisfactory comfort and gloss properties.

The hold of the composition is also improved; the composition does not migrate into the wrinkles and fine lines of the outline of the lips.

Although the present invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A cosmetic composition comprising, in a physiologically acceptable medium:
   one copolymer in the form of a block copolymer comprising a first block and a second block the first block and the second block are linked to one another by an intermediate block, wherein the first block is poly(isobornyl acrylate/isobornyl methacrylate) block the second block is poly(isobutyl acrylate/acrylic acid) block and an intermediate block is an isobornyl acrylate/isobornyl methacrylate/isobutyl 25 acrylate/acrylic acid,
   one non-volatile oil that has a hydrocarbon-based chain comprising at least 16 carbon atoms and having a molar mass of less than 650 g/mol; and
   one glossy oil having a molar mass of greater than or equal to 650 g/mol,
   wherein the block copolymer is in an amount of less than 40% by weight relative to the total weight of the composition.

2. The cosmetic composition according to claim 1, in which the non-volatile oil comprises an oil having a viscosity between 10 and 300 cPs.

3. The cosmetic composition according to claim 1, in which the non-volatile oil comprises a linear or branched, hydrocarbon-based oil having a molar mass of between 100 and 650 g/mol.

4. The cosmetic composition according to claim 1, in which the non-volatile oil is chosen from polyalkenes.

5. The cosmetic composition according to claim 4, in which the polyalkenes are chosen from polybutylenes, polydecenes, alkanes, and mixtures thereof.

6. The cosmetic composition according to claim 1, in which the non-volatile oil is squalane.

7. The cosmetic composition according to claim 1, comprising from 2% to 50% by weight of non-volatile oil, relative to the total weight of the composition.

8. The cosmetic composition according to claim 1, in which the glossy oil has a molar mass ranging from 650 to 10 000 g/mol.

9. The cosmetic composition according to claim 1, in which the glossy oil is chosen from:
   lipophilic polymers,
   esters,
   silicone oils,
   oils of plant origin,
   and mixtures thereof.

10. The cosmetic composition according to claim 1, in which the glossy oil is polybutylene.

11. The cosmetic composition according to claim 1, comprising from 5% to 50% by weight of at least one glossy oil, relative to the total weight of the composition.

12. The cosmetic composition according to claim 1, having an average gloss, measured at 20°, of greater than or equal to 35 and/or an average gloss, measured at 60°, of greater than or equal to 65.

13. The cosmetic composition according to claim 1, further comprising a dyestuff.

14. The cosmetic composition according to claim 1, said cosmetic composition being anhydrous.

15. The cosmetic composition according to claim 1, for caring for and/or making up the lips.

16. The cosmetic composition according to claim 1, in the form of a liquid gloss.

17. A cosmetic process for making up the lips, comprising the application to the lips of the cosmetic composition according to claim 1.

* * * * *